United States Patent
Iwamoto et al.

(10) Patent No.: US 6,200,582 B1
(45) Date of Patent: *Mar. 13, 2001

(54) LAMINATE HAVING ANTI-BACTERIAL AND MILDEWPROOFING ACTIONS

(75) Inventors: Eiji Iwamoto, Tokyo; Takeo Hayashi, Himeji; Toshimasa Onishi; Ikuya Tanaka, both of Tatsuno, all of (JP)

(73) Assignees: Idemitsu Petrochemical Co., Ltd., Tokyo; Nagase Chemicals Ltd., Osaka, both of (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/106,346

(22) Filed: Jun. 29, 1998

(30) Foreign Application Priority Data

Jun. 30, 1997 (JP) ...................................... 9-173657

(51) Int. Cl.⁷ .............................. B32B 5/18; B32B 27/18; A61K 9/70; A01N 31/08
(52) U.S. Cl. .......................... 424/404; 424/402; 514/365; 442/123; 442/124
(58) Field of Search ................................... 424/404, 402, 424/407; 514/365; 442/124, 123

(56) References Cited

U.S. PATENT DOCUMENTS 4,303,668 * 12/1981 Hasegawa et al. .................. 424/279
5,620,694 * 4/1997 Girardot et al. ..................... 424/402

OTHER PUBLICATIONS

Chemical Abstracts, vol. 101, No. 2, 1984, AN 8379, JP 59 025319, Feb. 9, 1984.

Chemical Abstracts, vol. 110, No. 24, 1989, AN 214426, JP 63 307937, Dec. 15, 1988.

Derwent Abstracts, AN 82–80239E, JP 57 131550, Aug. 14, 1982.

Derwent Abstracts, AN 82–10844E, JP 56 169054, Dec. 25, 1981.

Derwent Abstracts, AN 90–236634, JP 02 166075, Jun. 26, 1990.

* cited by examiner

*Primary Examiner*—Daniel Zirker
(74) *Attorney, Agent, or Firm*—Oblon, Spivak, McClelland, Maier & Neustadt, P.C.

(57) ABSTRACT

There is provided an anti-bacterial mildewproofing laminate, comprising at least two films or sheets each having organic substance permeability different from one another; and at least one adhesive layer which comprises an anti-bacterial mildewproofing agent containing parachlorometaxylenol as an active ingredient, and which intervenes between the adjacent films or sheets so that they are clad to one another. The above laminate exhibits durable anti-bacterial and mildewproofing actions without any special processing, is inexpensive, and shows anti-bacterial and mildewproofing actions even on surfaces out of contact with the laminate

6 Claims, No Drawings

LAMINATE HAVING ANTI-BACTERIAL AND MILDEWPROOFING ACTIONS

BACKGROUND OF THE INVENTION

1. Field of the Invention

The present invention relates to a laminate having anti-bacterial and mildewproofing actions, and more particularly to a laminate having anti-bacterial and mildewproofing actions such as a laminated film and a laminated sheet having anti-bacterial and mildewproofing actions, and a bag made of the same.

2. Description of the Related Arts

Recently, greater importance of an anti-bacterial and mildewproofing properties of various articles is emphasized not only in facilities wherein hygienic control is required, such as hospitals, but also in homes in general, and along therewith, impartment of anti-bacterial and mildewproofing actions to films, sheets, bags, and the like for packaging is demanded.

Conventionally, as films having an anti-bacterial effect, films are known that are made by mixing an inorganic type anti-bacterial agent containing a metal or metal ions in a synthetic resin. However, although the anti-bacterial effect of this type of films lasts long, this type of films has the defect that the effect is exhibited only on the surfaces brought into contact with the film.

On the other hand, a bag is suggested that contains an anti-bacterial agent of an organic substance (natural substance) type that exhibits an anti-bacterial effect also on surfaces not in contact therewith, but generally the effect of the anti-bacterial is poor in durability, and to make it durable, a special treatment such as microcapsulization is needed, leading to the defect that the cost is increased remarkably.

SUMMARY OF THE INVENTION

An object of the present invention is to provide a laminate that overcomes the above problems of the prior art, exhibits durable anti-bacterial and mildewproofing actions without any special processing, is inexpensive, and exhibits anti-bacterial and mildewproofing actions even on surfaces not in contact therewith.

The inventors of the present invention have intensively investigated with a view to aiming at the above object and have found that a laminate made by cladding films or sheets together using an adhesive or an adhesive resin containing parachlorometaxylenol (PCMX) out of various anti-bacterial and mildewproofing substances meets the above object. The present invention has been completed on the basis of that finding.

Namely, the present invention provides a laminate having anti-bacterial and mildewproofing actions, comprising at least two films or sheets each having organic substance permeability different from one another; and at least one adhesive layer which comprises an anti-bacterial mildewproofing agent containing parachlorometaxylenol as an active ingredient, and which intervenes between the adjacent films or sheets so that they are clad to one another.

DETAILED DESCRIPTION OF THE INVENTION

The films or sheets used in the present invention are not particularly restricted but may be selected from combinations of various films or sheets different from one another in organic substance permeability, such as synthetic resin films or sheets, paper molded items, fabrics, and metal films or sheets. Examples of the usable synthetic resin film or sheet include a film or sheet of a polyolefin such as a polyethylene and a polypropylene, a polyvinyl chloride, a polyvinylidene chloride, a polyamide such as nylon, a cellulose such as cellophane, a polyester such as a polyethylene terephthalate, or an ethylene/vinyl alcohol copolymer resin (EVOH). The pulp molded item includes, for example, an item of paper or a synthetic paper. Examples of the metal for the film or sheet include aluminum, copper, iron, and a stainless steel, which are used, for example, in the form of aluminum foil.

The combination includes a combination of synthetic resins and a combination of a synthetic resin with paper, a pulp molded item, a fabric, or a metal. The greater the difference in organic substance permeability in the films or sheets of the combination is, the more the anti-bacterial and mildewproofing actions on one of the films or sheets is expected, which is effective.

By way of parenthesis, herein, the term "organic substance permeability" means permeability of a gas composed of an organic substance, such as PCMX gas.

Parachlorometaxylenol used as an anti-bacterial mildewproofing agent is low in vapor pressure (the vapor pressure: 0.0033 mmHg at 20° C.) and less sublimable at normal temperatures and keeps its anti-bacterial and mildewproofing effect for a long period of time. Accordingly, the intended object can be satisfactorily attained only by lamination without requiring any special processing such as microcapsulization. Thus, an inexpensive laminate can be provided.

The laminate of the present invention is one obtained by incorporating parachlorometaxylenol in an intervening adhesive layer that clads at least two films or sheets different from one another in organic substance permeability.

As the lamination method, a variety of lamination methods can be employed, which can be suitably selected in accordance with the combination of the films or sheets that are clad to one another, and examples are a dry lamination method, a wet lamination method, an extrusion sandwich lamination method, a wax coater lamination method, and a hot-melt lamination method.

Since parachlorometaxylenol dissolves quickly in ethyl acetate that is a solvent for dry lamination (87 g/100 ml at 25° C.), it is dispersed uniformly in the dry lamination process and the effect can be expected throughout the laminate surfaces.

Further, since, in the wet lamination method, a solution type or emulsion type adhesive wherein parachlorometaxylenol is dispersed uniformly can be prepared, a uniform anti-bacterial and mildewproofing effect can be obtained.

Furthermore, the sandwich lamination method can be applied and, in this case, an anti-bacterial mildewproofing agent containing parachlorometaxylenol as an active ingredient is mixed in an adhesive agent and the mixture can be used by heating-melting.

The adhesive and the adhesive resin are not particularly restricted but can be suitably selected in accordance with the films or sheets that will be clad to one another.

The laminate of the present invention contains, in an adhesive layer, an anti-bacterial mildewproofing agent whose active ingredient is parachlorometaxylenol, and preferably the content of parachlorometaxylenol in the adhesive layer is 0.1 to 60% by weight (the content of parachlorometaxylenol in the laminate is 0.002 to 1.35 g/m$^2$). If the content of parachlorometaxylenol is less than 0.1% by weight, a satisfactory anti-bacterial and mildewproofing effect cannot be secured, whereas if the content is more than 60% by weight, there arises the problem that the adhesion strength between the films is lowered.

Further, the anti-bacterial mildewproofing agent can contain, in addition to the above active ingredient, a variety of additive components if desired.

Since the laminate of the present invention contains an anti-bacterial mildewproofing agent in an adhesive layer, if one comes in direct contact with the laminate, there is no fear that one comes in direct contact with a large amount of the anti-bacterial mildewproofing agent and therefore the laminate is high in safety. Furthermore, parachlorometaxylenol is an anti-bacterial mildewproofing agent high in safety since its acute toxicity is 3,450 mg/kg or more (orally, rats).

Since the laminate of the present invention contains an anti-bacterial mildewproofing agent in an adhesive layer, the gaseous sublimate of the anti-bacterial mildewproofing agent sublimed from the adhesive layer exhibits the anti-bacterial and mildewproofing effect and therefore the anti-bacterial and mildewproofing effect can be expected at parts not in contact with the laminate.

In the case where the laminate is made into a bag, the anti-bacterial and mildewproofing effect can be expected throughout the inside of the bag. Further, by using a film good in permeability on the inside of a bag, a bag can be obtained wherein the anti-bacterial and mildewproofing effect is exhibited preferentially for the inside of the bag. A laminate wherein the outer layer is a laminate of a metal, such as aluminum, can exhibit its anti-bacterial and mildew-proofing effect selectively only on the inside.

In the following, the present invention will be described in more detail with reference to Examples, which however shall not limit the present invention thereto.

EXAMPLE 1

A laminate film was prepared by the dry lamination method using a biaxially oriented nylon film for the face base and a $C_8$ series straight-chain low-density polyethylene film for the back base. At that time, as an adhesive, a generally used ether type adhesive was used, to which was added 15% by weight of parachlorometaxylenol dissolved in ethyl acetate based on the adhesive. The laminating was carried out under the same conditions as used in general, except that the anti-bacterial mildewproofing agent was added to the adhesive.

The anti-bacterial and mildewproofing effect of the obtained laminate film was evaluated in accordance with the following methods:

(1) Mildewproofing Effect Test

A potato dextrose agar medium inoculated with a suspension of mixed spores of four fungi (*Aspergillus niger, Penicillum citrinum, Cladosporium cladosporiodes,* and *Chaetromium globosum*) by spraying was placed in a bag (250×290 mm) made of the above laminate film. After the bag was allowed to stand at a temperature of 28° C. for 4 weeks, the state of the growth of the fungi was observed. The results were evaluated according to the following criteria. The results are shown in Table 1.

Evaluation Criteria:

0: The growth of the hyphae was not observed on the medium.

1: The area of the medium where the growth of the hyphae was observed was not more than ⅓ of the total area of the medium.

2: The area of the medium where the growth of the hyphae was observed was more than ⅓ of the total area of the medium.

TABLE 1

| | State of growth of fungi | |
|---|---|---|
| Sample | After 2 weeks | After 4 weeks |
| Laminate film of the present invention | 0 | 0 |
| Laminate film with no additive | 2 | 2 |

While, in the bag made of the laminate film to which the anti-bacterial mildewproofing agent was not added, the area of the medium where the growth of the hyphae was observed was more than ⅓ of the total area of the medium, the growth of the hyphae was not observed on the medium stored in the bag made of the laminate film of the present invention even after 4 weeks. From the results, it was confirmed that the laminate film of the present invention exhibited clearly a mildewproofing effect even at a part where the film is not in direct contact.

(2) Anti-bacterial Effect Test

*Staphylococcus aureus* which had been shake-cultured at 30° C. for 16 hours was suspended in a ¹⁄₁,₀₀₀ times diluted broth medium to prepare an organism liquid of $10^6$ CFU/ml, the organism liquid was inoculated between two of the above laminate films cut to 50×50 mm each, both surfaces were brought in close contact with each other, and the cultivation was carried out at 35° C. for 48 hours. Thereafter, the organism liquid was washed out with 10 ml of a soybean/casein digest (SCDLP) liquid medium to which lecithin and polysorbate 80 were added, into a sterilized petri dish, and the viable cell count was determined by the agar dilution plate method of a standard agar medium. The results are shown in Table 2. From the results it was confirmed that the laminate film of the present invention had a satisfactory bacteriostatic effect on *Staphylococcus aureus*.

TABLE 2

| | Viable cell count (CFU/ml) | |
|---|---|---|
| Sample | Initial stage | After 48 hours |
| Laminate film of the present invention | $4.5 \times 10^8$ | 10 or less |
| Laminate film with no additive | $4.5 \times 10^8$ | $5.1 \times 10^7$ |

Comparative Example

The anti-bacterial and mildewproofing actions of specimens of the commercially available items shown in Table 3 was tested in accordance with the method shown below.

TABLE 3

| Sample No. | Name of sample (trade name) | Anti-bacterial agent (% by weight) |
|---|---|---|
| 1 | Unilon G100 | none |
| 2 | Unilon G100 | 15[*1] |
| 3 | Uniaslon HP7000 | 10[*1] |
| 4 | Uniaslon TB1000 | 10[*1] |
| 5 | Item into which a thiazolyl sulfamide compound is incorporated | — |
| 6 | Item into which a silver-based anti-bacterial agent is incorporated | — |

[*1]: Parachlorometaxylenol was used as an anti-bacterial agent.

Test Method (1) Anti-bacterial Potency Test 10 ml of a bouillon medium was distributed into each L-shaped test tube and each of the specimens cut to a size of 50×20 mm was immersed in the medium of each test tube. Staphylococcus aureus which had been shake-cultured at 30° C. for 16 hours was adjusted to $10^6$CFU/ml and 0.1 ml of this organism liquid was added dropwise in each of the L-shaped test tubes. The organism liquid was shake-cultured (shake rate: 60 rpm) at 30° C. for 48 hours and the absorbance at 660 nm was measured with the passage of time to find the increase in the cell count. The results of the measurement after 24 hours are shown in Table 4. As is understood from the results, the propagation of Staphylococcus aureus was suppressed, except Sample Nos. 1 and 2.

TABLE 4

| Sample No. | $OD_{660}$* |
|---|---|
| 1 | 2.8 |
| 2 | 0.0 |
| 3 | 0.0 |
| 4 | 0.0 |
| 5 | 0.0 |
| 6 | 2.5 |

*absorbance at 660 nm (2) Mildewproofing Potency Test

An artificial sweat was prepared in accordance with JIS L0848-1978. After a piece of sterilized gauze was immersed in the artificial sweat to absorb the artificial sweat sufficiently, the piece was taken out, was wiped off slightly, and was used as a test piece. This test piece was placed on a carbon-free inorganic salt medium, and a suspension of mixed spores of four fungi (Aspergillus niger, Penicillum citrinum, Cladosporium cladosporiodes, and Chaetromium globosum) was sprinkled thereon to form each medium for evaluation. Each of the mediums for evaluation was placed in each of the specimens and was stored at 28° C. After 2 weeks, the state of the growth of hyphae produced on the test pieces was observed and the mildewproofing effect was evaluated in accordance with the following criteria. The results are shown in Table 5.

Evaluation Criteria:

0: No growth of hyphae was observed on the test piece.
1. The area where the growth of hyphae was observed on the test piece was not more than ⅓ of the total area of the test piece.
2. The area where the growth of hyphae was observed on the test piece was more than ⅓ of the total area of the test piece.

TABLE 5

| Sample No. | State of growth |
|---|---|
| 1 | 2 |
| 2 | 0 |
| 3 | 0 |
| 4 | 0 |
| 5 | 2 |
| 6 | 2 |

The laminate of the present invention can be produced by the usual laminating process only without requiring any special processing and is therefore inexpensive. Further, since the vapor pressure of parachlorometaxylenol that is an active ingredient of the anti-bacterial mildewproofing agent to be used is low, it is less sublimable at normal temperatures and the anti-bacterial and mildewproofing actions last long. Further, since the parachlorometaxylenol is an anti-bacterial mildewproofing agent low in acute toxicity and high in safety and is incorporated in an adhesive layer, even if one comes in direct contact with the laminate, there is no fear that one comes in direct contact with a large amount of the anti-bacterial mildewproofing agent, thus assuring high safety of the laminate.

Further, since the laminate of the present invention contains an anti-bacterial mildewproofing agent incorporated in an adhesive layer, the sublimated gas of the agent sublimated from the adhesive layer exhibits the anti-bacterial effect and therefore the anti-bacterial and mildewproofing effect can be exhibited even at parts out of contact with the laminate.

Further, in the case wherein the laminate is made into a bag, the anti-bacterial and mildewproofing effect can be expected throughout the inside of the bag. Furthermore, a bag having an anti-bacterial and mildewproofing effect preferentially for the inside of the bag can be obtained by using a film good in permeability on the inside of the bag.

What is claimed is:

1. A bag comprising, a bag having anti-bacterial and mildew proofing actions, comprising at least two films or sheets each of the films or sheets having different permeability to an organic substance, and one of said films or sheets being on the inside of the bag and having better permeability to said organic substance; and at least one adhesive layer which comprises an anti-bacterial and mildew-preventing agent containing para-chloro-meta-xylenol as an active ingredient, wherein said para-chloro-meta-xylenol is dissolved in ethyl acetate; and wherein said adhesive layer intervenes between the adjacent films or sheets so that the films or sheets are arrayed on to one another;

wherein 0.1 to 15% by weight of p-chloro-m-xylenol is contained in said adhesive layer; and wherein the content of p-chloro-m-xylenol in the bag is from 0.002 to 1.35 g/m².

2. The bag as claimed in claim 1, wherein said films or sheets comprise at least one material selected from the group consisting of synthetic resins, paper, fabrics, and metals.

3. The bag as claimed in claim 1, wherein one of the two films or sheets to be arrayed on to one another is a metal foil.

4. The bag as claimed in claim 1, wherein one or both of the two films or sheets to be arrayed on to one another are made of paper.

5. The bag as claimed in claim 1, wherein the films or sheets are arrayed on to one another by a dry lamination method or a wet lamination method using an adhesive incorporated with said anti-bacterial mildew-preventing agent.

6. The bag as claimed in claim 1, wherein the films or sheets are arrayed on to one another by an extrusion sandwich lamination method using an adhesive incorporated with said anti-bacterial mildew-preventing agent.

* * * * *